United States Patent [19]

Sekiguchi

[11] Patent Number: 4,878,750

[45] Date of Patent: Nov. 7, 1989

[54] OPHTHALMIC MEASURING APPARATUS

[75] Inventor: Kyoji Sekiguchi, Tokyo, Japan

[73] Assignee: Canon Kabushiki Kaisha, Tokyo, Japan

[21] Appl. No.: 318,474

[22] Filed: Mar. 3, 1989

Related U.S. Application Data

[63] Continuation of Ser. No. 820,801, Jan. 22, 1986, abandoned.

[30] Foreign Application Priority Data

Jan. 25, 1985 [JP] Japan .................................. 60-13161
Feb. 9, 1985 [JP] Japan .................................. 60-23728

[51] Int. Cl.$^4$ ............................................... A61B 3/10
[52] U.S. Cl. .................................... 351/212; 351/205
[58] Field of Search ................. 351/205, 206, 211, 212

[56] References Cited

U.S. PATENT DOCUMENTS 4,312,574 1/1982 Wilms ............................... 351/212
4,431,278 2/1984 Nohda ............................... 351/211

FOREIGN PATENT DOCUMENTS

29446 2/1983 Japan .

Primary Examiner—Rodney B. Bovernick
Assistant Examiner—P. M. Dzierzynski
Attorney, Agent, or Firm—Fitzpatrick, Cella, Harper & Scinto

[57] ABSTRACT

An ophthalmic measuring apparatus has a corneal shape measuring system projecting a first target image onto the cornea of an eye to be examined and receiving the corneal reflection image of the first target image by a first photodetector device to obtain information on the corneal shape, a refractive power measuring system projecting a second target image onto the eye fundus of the eye to be examined and receiving the corneal reflection image of the second target image by a second photodetector device to obtain information on the refractive power of the eye, a signal processing device selectively receiving the output of the corneal shape measuring system or the refractive power measuring system to calculate the corneal shape or the refractive power of the eye, and a measuring mode selecting device connected to the signal processing device to select a single measurement of the corneal shape of refractive power of the eye, or successive measurements of both.

20 Claims, 8 Drawing Sheets

Fig. 19(a)
AVR = 8.56
< HARD >  <  SOFT  >
A  B  C  D  E  F  G  H

Fig. 19(b) AVR = 8.56
<  HARD >  <xx SOFT xx>
A  B  C  D  E  F  G  H

Fig. 19(c) AVR = 8.56
<xx HARD xx>   <- -SOFT- ->
A  B  C  D  E  F  G  H

OPHTHALMIC MEASURING APPARATUS

This application is a continuation of application Ser. No. 820,801, filed Jan. 22, 1986, now abandoned.

BACKGROUND OF THE INVENTION

1. Field of the Invention

The present invention relates to an ophthalmic measuring apparatus capable of measuring the corneal shape and the eye refractive power in a single unit.

2. Description of the Prior Art

At an examination of eye refractive power, measurement of the corneal shape is usually carried out in addition to the measurement of refractive power, for the purpose of examining the presence of astigmatism and the axis and degree thereof. Particularly because of the recent popularity of contact lenses, the examination of corneal shape has become more important for selecting the base curve of the contact lenses.

Heretofore, at such examination for prescribing a contact lens, it has been customary to measure the corneal shape of the examinee with an instrument called ophthalmometer or keratometer thereby selecting the base curve and determining the degree of corneal astigmatism, then to determine the full refractive power and the full astigmatism by an unconscious (objective) refraction examination with a refractometer or the like, and to effect a self-conscious (subjective) refraction examination and final determination of the base curve by the trial lens method.

As described above, the measurements of shape of cornea and of refractive power have heretofor been carried out with different instruments and have therefore required considerable time and labor for both of the examiner and examinee.

Hard contact lens and soft contact lens have different characteristics in the correction of astigmatism. The hard contact lens can correct the corneal astigmatism to a certain degree by a correcting effect of a layer of tear formed between the lens and cornea. On the other hand, the soft contact lens is unable to correct astigmatism since it follows the curve of cornea.

Such advantage of hard contact lens can, however, appear as a drawback in certain cases. The astigmatism of an eye can be composed of corneal astigmatism and lenticular astigmatism, which might mutually compensate. In case of such an eye, the use of a hard contact lens will result in the correction of corneal astigmatism only, whereby the remaining lenticular astigmatism becomes manifested, thus aggravating the overall astigmatism. Consequently, in prescribing a contact lens, attention should be paid not only to the near- and far-sightedness but also to the astigmatism.

In prescribing a contact lens, it has been customary, as explained above, to measure the shape of cornea with an ophthalmometer or a keratometer to select the base curve and determine the degree of corneal astigmatism, then to screen the full refractive power and the full astigmatism by an unconscious refraction examination with a refractometer or the like, and to effect a self-conscious refraction examination and final determination of the base curve by the trial lens method.

In such an examination, the examiner tries a trial lens from a flatter one to a strongly curved one, according to the average radius of curvature of cornea obtained by the ophthalmometer or auto-kerato-meter and referring to a table separately prepared by the examiner, to determine a contact lens matching the examined eye. However, in such a method, the time and labor required until final determination of a suitable contact lens are considerable burdens to both of examiner and examinee.

In order to resolve such a problem, there is already known an ophthalmometer or a keratometer which which incorporates a computer that prints a lens matching the average radius of curvature of the cornea through selection from a list likewise incorporated in such an instrument. Such an instrument is further provided with a function to select a soft contact lens according to the degree of the lenticular astigmatism, but an optimum contact lens cannot be prescribed in a certain case unless attention is also paid to the remaining astigmatism as explained before.

SUMMARY OF THE INVENTION

An object of the present invention is to provide an inexpensive and compact ophthalmic measuring apparatus capable of measuring and computing the eye refractive power and the corneal shape with same signal processing means in addition to a single measurement of the refractive power or the corneal shape, thereby significantly reducing the time and labor required for such measurements.

Another object of the present invention is to provide an ophthalmic measuring apparatus capable of measuring the eye refractive power and the corneal shape with a same instrument and furhter provided with a function of selecting contact lenses, whereby a contact lens adequately matching the examined eye can be selected within a short time, according to the results obtained by consecutive measurements of the refractive power and corneal shape.

DESCRIPTION OF THE PREFERRED EMBODIMENTS

Figure 1:
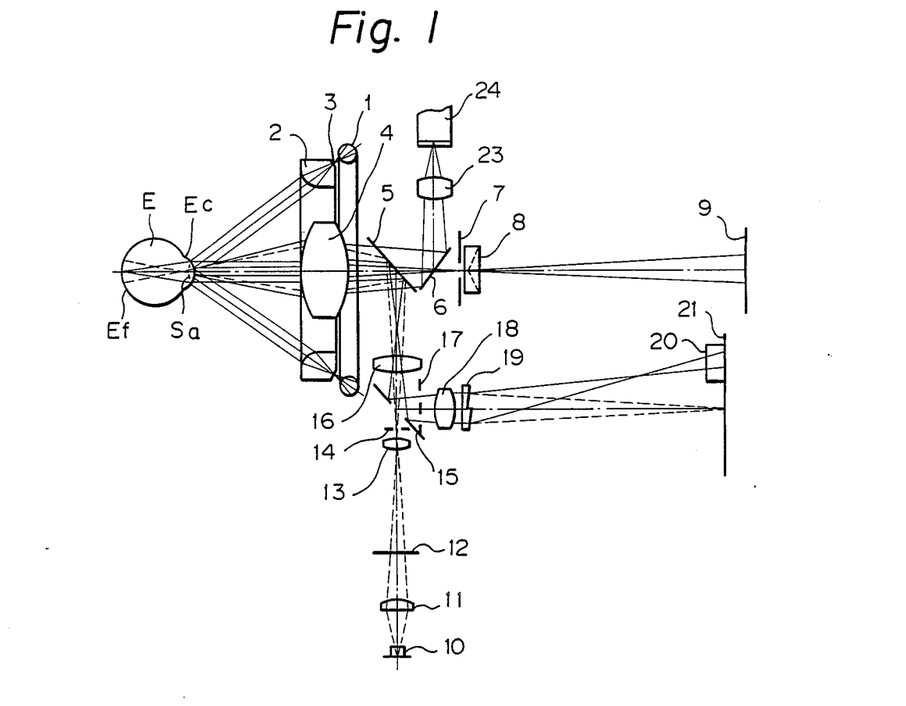
FIG. 1 shows optical construction of a first embodiment of the present invention.

FIG. 1 shows an optical system according to an embodiment of the present invention. During measurement of the shape of cornea, a visible light emitted from an annular strobe light 1 illuminates a circular slit 3 positioned opposite to an eye to be examined, with respect to a collimating ring lens 2. Said slit 3, when viewed in a cross-section containing the optical axis, lies on the focal plane of said ring lens 2, so that the cornea Ec of said eye E is illuminated by the light projected from said slit 3 positioned at the optically infinite point. Since the surface of the cornea Ec is shaped like a convex mirror, there is formed a corneal reflection image Sa of the slit 3, which is transmitted through an objective lens 4, a dichroic mirror 5 transmitting visible light and reflecting infrared light, a half mirror 6 and a multi-apertured stop plate 7, then deflected by a prism 8 and refocused on a linear position detecting element 9.

Figure 2A:
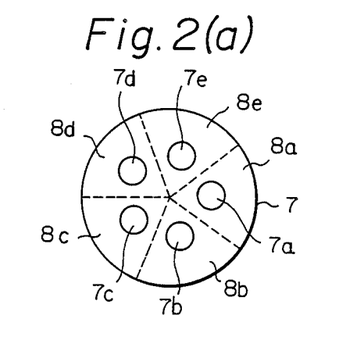
FIG. 2(a) is a front view of a multi-apertued stop.
Figure 2B:
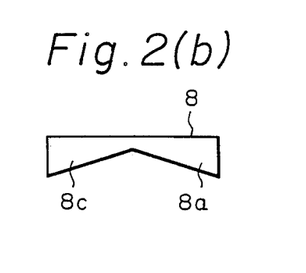
FIG. 2(b) is a cross-sectional view of a prism.
Figures 3, 4, 5, 6:
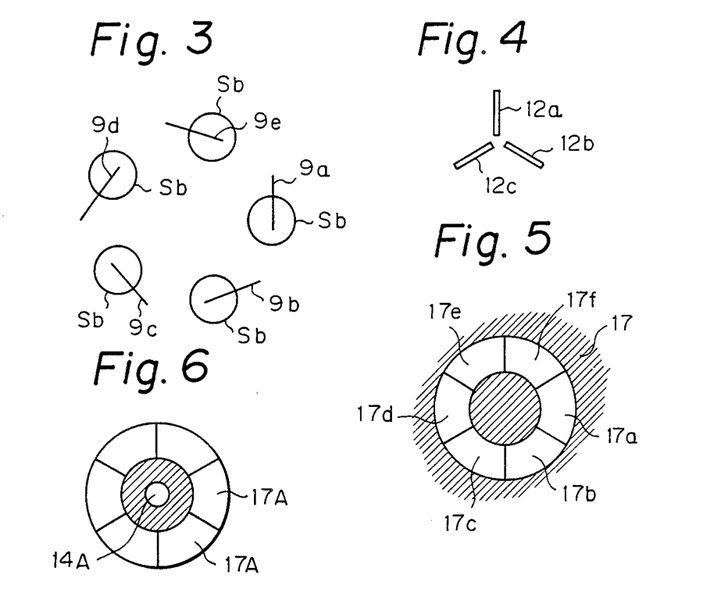
FIG. 3 is a schematic view showing the relation between the corneal reflection image and a detection element.
FIG. 4 is a front view of an eye fundus projection chart.
FIG. 5 is a front view of an aperture plate for measuring the eye refraction.
FIG. 6 is a front view showing the imaged condition of the stop on a pupil of an eye to be examined.

As shown in FIG. 2(a), the multi-apertured stop 7 is provided for example with five apertures 7a–7e, and the prism 8 is divided into corresponding five elements 8a–8e, as indicated by broken lines in FIG. 2(a), each of which has a cross section as shown in FIG. 2(b). Five corneal reflection images separated by said multi-apertured stop 7 and prism 8 are coupled together at the position of the detection element 9 in a relation as shown in FIG. 3. In FIG. 3 Sb designates corneal reflection images into which the corneal reflection image Sa is imaged and separated by the objective lens 4, and reference characters 9a–9e denote detecting elements which respectively correspond to the apertures 7a–7e and the prism elements 8a–8e. Thus the coordinates of five points in the corneal reflection images Sb are detected, and the coordinates of these five points are substituted into the following general equation of quadratic curve:

$$AX^2+BXY+CY^2+DX+EY+F=0$$

to thereby solve simultaneous equations, whereby coefficients A–E are found and modified into the following general equation of ellipse:

$$(x-x_0)^2/a^2+(y-y_0)^2/b^2=1$$

where
$x = X \cos\theta - Y \sin\theta$
$y = X \sin\theta - Y \cos\theta$
whereby the radii of curvature of the two main meridians of the cornea Ec are derived from the major axis a and the minor axis b of the ellipse and, thus, the axis of astigmatism can be calculated from the angle $\theta$.

On the other hand, where the refractive power is to be measured, as shown in FIG. 1, the light from an infrared light emitting diode 10 passes through a condensing lens 11 and illuminates an eye fundus projecting chart 12. Said chart 12, as shown in FIG. 4, is provided with three slits 12a–12c radially extending with an interval of 120°. The light from the light-emitting diode 10 passes further through a relay lens 13, is then once focused on an eye fundus illuminating stop 14, then passes through an aperture mirror 15 and a relay lens 16, reflected by the infrared-reflecting dichroic mirror 5, imaged on the pupil of the eye E to be examined through the objective lens 4 and illuminates the eye fundus.

Also the chart 12 is once focused through the relay lenses 13 and 16 and projected by the objective lens 4 so as to be optically conjugate with the fundus of an eye in emmetropia. The reflected image from the eye fundus again passes through the objective lens 4 and is reflected and imaged by the dichroic mirror 5, and further passes through the relay lens 16 and is reflected by the apertured mirror 15. An aperture plate 17 is disposed near the apertured mirror 15, and is provided with six openings 17a–17f as shown in FIG. 5. The openings 17a and 17d, 17b and 17e, 17c and 17f respectively form channels. The eye fundus illuminating stop 14 and the aperture plate 17 are focused on the pupil of the eye E to be examined as indicated by 14A and 17A in FIG. 6, so as to separate the projecting system and the measuring system of the chart 12.

Figures 7A, 7B:
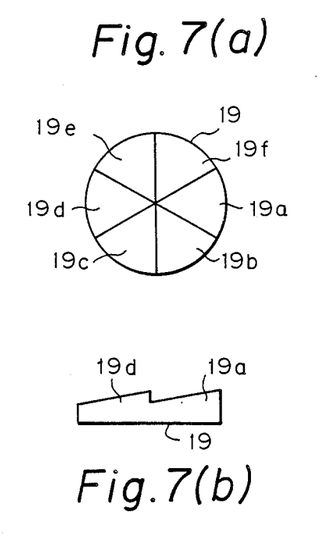
FIG. 7(a) is a front view of an image separating prism for measuring the refractive power.
FIG. 7(b) is a cross-sectional view thereof.

The light flux divided by the aperture plate 17 is deflected by a prism 19 through an imaging lens 18, is then condensed in the transversal direction to a detecting element 21 by a cylindrical lens 20 and is focused on three detecting elements 21a–21c. The prism 19 is provided with six elements 19a–19f as shown in FIG. 7(a) and is adapted to separate the images corresponding to the six openings 17a–17f of the aperture plate 17. FIG. 7(b) shows the cross-sectional shape of the prism 19.

Figure 8:
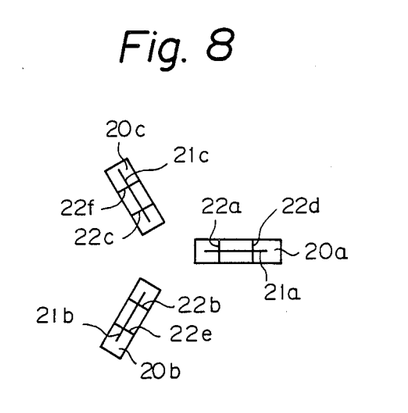
FIG. 8 is a schematic view showing the relation between the image of the eye fundus and a detecting element.

The images thus separated are condensed longitudinally by three cylindrical lenses 20a–20c and focused on the detecting elements 21a–21c. FIG. 8 shows the imaged conditions of the images of the eye fundus, wherein indicate the images of the eye fundus corresponding to the openings 17a–17f.

If the eye E to be examined is out of emmetropia, the light ray leaving the eye fundus and passing through a certain point of the pupil emerges at an angle corresponding to the refractive power so that, with an optical system as in the present embodiment, the interval between the two eye fundus images 22 on the detecting element 21 will vary in accordance with the refractive power of the eye E to be examined. Consequently, if the relation between the interval of the two eye fundus images 22 and the refractive power is found in advance, the refractive powers in three meridian directions can be measured, and it is rendered possible to determine the refractive power, the degree and angle of astigmatism by substituting each of those refractive powers into the following equation:

$$D = A \sin^2(\omega+\theta)+B$$

wherein variables D and $\omega$ respectively represent the refractive power and the angle of meridian direction, and constants A, B and $\theta$ respectively stand for the degree of astigmatism, average refractive power and axis of astigmatism.

The alignment between the eye E to be examined and the instrument can be accomplished by focusing the light from the front eye part, transmitted through the objective lens 4 and dichroic mirror 5 and reflected by the half mirror 6, on a television image pickup tube 24 by a television relay lens 23 and monitoring the image by a television monitor connected to said image pickup tube 24.

Once the eye retractive power and the corneal shape are determined, the degree of remaining astigmatism may be obtained by subtracting the corneal astigmatism from the total astigmatism. Among the degree of total astigmatism Ct of eye refractive power, the corresponding axis AXt, the degree of corneal astigmatism Cc, the corresponding axis Axc, the degree of remaining astigmatism Cr, and the corresponding axis AXr, there stand following relations:

$$Cr \sin 2AXr = Ct \sin 2AXt - Cc \sin 2AXc$$

$$Cr \cos 2AXr = Ct \cos 2AXt - Cc \cos 2AXc$$

so that:

$$AXr = (1/2)\tan^{-1} \frac{(Ct \sin 2AXt - Cc \sin 2AXc)}{(Ct \cos 2AXt - Cc \cos 2AXc)}$$

$$Cr = \frac{(Ct \sin 2AXt - Cc \sin 2AXc)}{\sin 2AXr}$$

The degree of remaining astigmatism Cr of eye refraction is useful in prescribing a contact lens or an eyeglass. In fact it is important information for the examiner in prescribing a contact lens, since the corneal astigmatism is correctable to a certain extent with a contact lens, so that, in case the eye E to be examined has a total astigmatism, the magnitude of the degree of remaining astigmatism Cr allows to determine whether the correction with a contact lens is possible.

Figure 9:
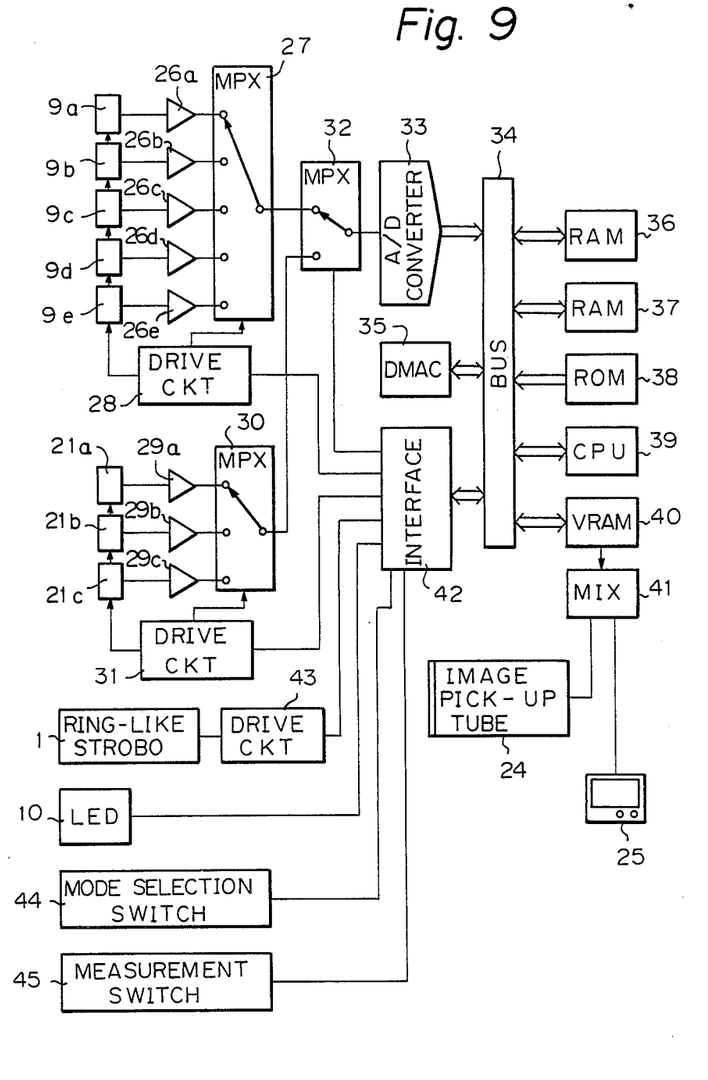
FIG. 9 is a block diagram of the circuit.

FIG. 9 is a block diagram of a control device for obtaining such information in the present embodiment. Said control device is composed of two head amplifier blocks, a control block and a peripheral block. In the first head amplifier block for corneal shape measurement, the detecting elements 9a-9e are respectively connected to amplifiers 26a-26e which are connected to a first analog multiplexer (MPXI) 27, and a detecting element driving circuit 28 is connected to said detecting elements 9a-9e and said MPXI 27.

The second head amplifier block for eye refraction measurement has a similar structure to that of said first block, wherein the detecting elements 21a-21c are respectively connected to amplifiers 29a-29c which are connected to a second analog multiplexer (MPXII) 30, and a detecting element driving circuit 31 is connected to said detecting elements 21a-21c and to said MPXII 30.

In a third block for processing, storing and controlling the outputs from the first and second blocks, a third analog multiplexer (MPXIII) 32 connected to said MPXI 27 and MPXII 30 supplies as output to a computer bus 34 through an A/D converter 33. Also connected to said computer bus 34 are a direct memory access controller (DMAC) 35, a first random access memory (RAMI) 36, a second random access memory (RAMII) 37, a read-only memory (ROM) 38, a central processing unit (CPU) 39 and a video random access memory (VRAM) 40. To said VRAM 40 there is connected a mixer (MIX) 41 which is in turn connected to a television image pickup tube 24 and a television monitor 25.

A fourth block is composed of circuits connected to an interface 42 which is connected to said computer bus 34. To said interface 42 there are connected detecting element driving circuits 28, 31, said MPXIII 32, a strobo driving circuit 43 connected to the ring strobo light 1, the light-emitting diode 10, a measuring mode selector switch 44 and a measuring switch 45.

Corneal shape signals detected by the detecting elements 9a-9e are amplified by the amplifiers 26a-26e, and supplied to the MPXIII 32 by successive selection by the MPXI 27. The detecting element driving circuit 28 generates timing signals for controlling the signal readout from the detecting elements 9a-9e and the successive switching of the MPXI 27.

Similarly the detecting element driving circuit generates timing signals for controlling the signal readout from the detecting elements 21a-21c and the successive switching in the MPXII 30, whereby eye refraction signals detected by said elements are amplified by the amplifiers 29a-29c and supplied to the MPXIII 32 by selection of the MPXII 30.

The analog signals from the first and second blocks are alternately switched in the MPXIII 32, and supplied to the computer bus 34, after conversion into digital signals by the A/D converter 33, for the following processes by the circuits connected to bus 34. The DMAC 35 controls the data storage to store the data of the corneal reflection images in the RAMI 36 and to store the data of the eye fundus reflection images in the RAMII 37. The CPU 39 performs calculation and control according to the sequence and calculation procedure of the entire apparatus stored in the ROM 38, and the results of processing in the CPU 39 are stored in the VRAM 40. The signals therefrom and the image of the front eye part of the eye E to be examined, captured by the image pickup tube 24, are displayed on the television monitor 25 through the MIX 41.

Signals from the measuring switch 45 and the measuring mode selector switch 44 are supplied to the interface 42, which controls the light-emitting diode 10, strobo driving circuit 43, detecting element driving circuit 28, 31 and MPXIII 32 according to instructions of the CPU 39 transmitted through the computer bus 34.

In the present embodiment amplifiers 26a-26e, 29a-29c are provided respectively corresponding to the detecting elements 9a-9e, 21a-21c. The amplifiers 26, 29 have to be provided close to the detecting elements 9a-9e, 21a-21c, since otherwise the weak output signals thereof are easily affected by clock noises from the detecting element driving circuits 28 and 31 and are unable to provide sufficiently high S/N ratios, and for this reason, the amplifiers 26a-26e, 29a-29c of the same number as that of the detecting elements 9a-9e, 21a-21c. are required. Theoretically the MPXI 27 and MPXII 30 may be placed in front of an amplifier 26 and an amplifier 29 to reduce the number of amplifiers in this manner, but the S/N ratios will be deteriorated since the characteristics of the MPXI 27 and MPXII 30 in the weak signal range are considerably inferior. For this reason it is preferably to employ the amplifiers 26a-26e, 29a-29c in front of the MPXI 27 and MPXII 30. Also the amplifiers 29a-29c have to have high gains since the reflected light from the eye fundus Ef is extremely weak, and the structure of the present invention is preferably also for compensating the difference in the outputs of the detecting elements 21a-21c.

Figure 10:
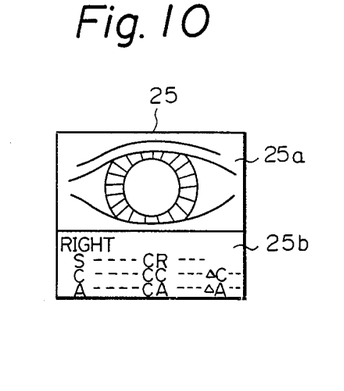
FIG. 10 is a front view of an image of a television monitor.

FIG. 10 shows the mode of display of the eye refraction and corneal shape on the television monitor 25, wherein an upper part 25a of the frame displays the external appearance of the eye to be examined while a lower part 25b displays the results of calculation. FIG. 10 shows a case of examining a right eye, and the refractive power of the eye is represented by the spherical refractive power S, degree of total astigmatism C and angle A of axis, while the shape of cornea is represented by the radius CR of corneal curvature, degree of corneal astigmatism CC and angle CA of axis. Also there are displayed the degree of remaining astigmatism ΔC obtained subtracting the corneal astigmatism CC from the total astigmatism C, and the angle of axis ΔA of said remaining astigmatism.

Figure 11:
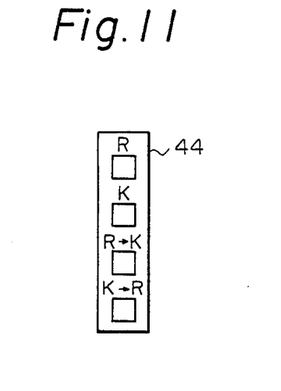
FIG. 11 is a front view of a measuring mode selector switch board.

FIG. 11 shows an embodiment of the measuring mode selector switch 44, containing an eye refraction measuring mode switch R, a corneal shape measuring mode switch R, a mode switch R→K for an eye refraction measurement followed by a corneal shape measurement, and a mode switch K→R for a corneal shape measurement followed by an eye refraction measurement.

Figure 12:
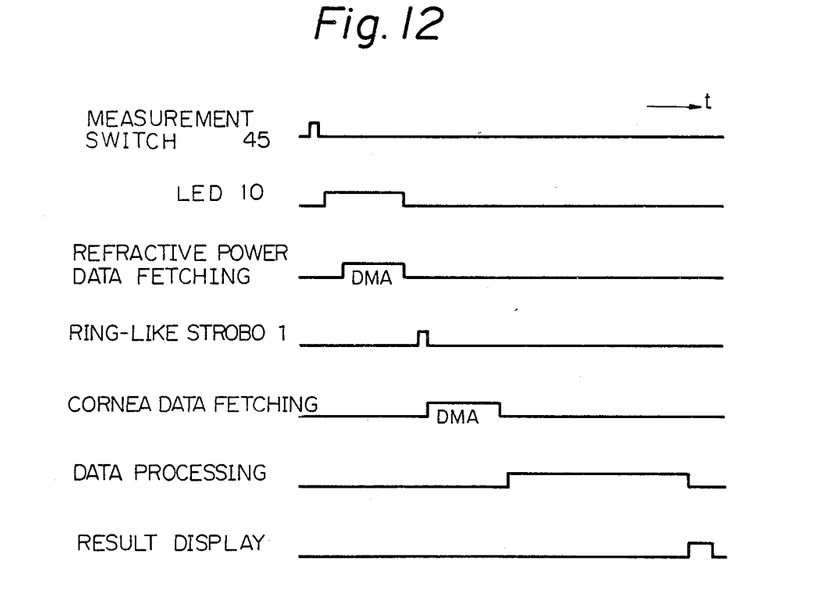
FIG. 12 is a timing chart showing the timing of measurement.

FIG. 12 is a timing chart showing the timings of measurements in a mode R→K for measuring the eye refraction and corneal shape. As the selector switch 44 is in a state R→K, the MPXIII 32 is connected for measuring the eye refractive power, and, upon actuation of the measuring switch 45, the light-emitting diode 10 is activated and the signals are stored in the detecting elements 21a-21c for several tens of milliseconds. Then the data of the eye fundus images 22a-22f entered to the detecting elements 21a-21c are selected in succession by the MPXII 30, and digital signals obtained in the A/D converter 33 are directly stored in the RAM 136 under the control of the DMAC 35. Upon completion of the data reading of the eye fundus images 22a-22f, the MPXIII 32 is switched over for measuring the corneal shape, whereupon, in response to a signal from the interface 42, the strobo driving circuit 43 activates the ring strobo light 1 and the corneal reflection images thus formed are stored in the detection elements 9a-9e. Thus accumulated signals are selected in succession by the MPXI 27, then converted into digital signals by the A/D converter 33 in the same manner as in the measurement of the eye refractive power, and directly stored in the RAMII 37 by the DMAC 35. Upon completion of these two data retrievals, the CPU 39 performs calculations according to a procedure stored in the ROM 38 and displays the results of calculations of the eye refractive power and the shape of cornea on the television monitor 25.

In case of a single measurement, the eye refractive power or the corneal shape can be singly measured by selecting the mode R or K with the mode selector switch 44, but the other measurement, if necessitated in the course of examination, can be effected by depressing the button K or R. If the button K is depressed later when the button R is depressed at first, the data of eye refraction measured at first are stored in the RAMI 36 and a measurement of corneal shape is conducted in succession, thereby obtaining results of both measurements as if a switch R→K is initially selected. Also in case the button R is depressed later when the button K is depressed at first, the data of corneal shape are stored in the RAMII 37 and the results are obtained in the similar procedure as if the switch K→R is selected at first.

Figure 13:
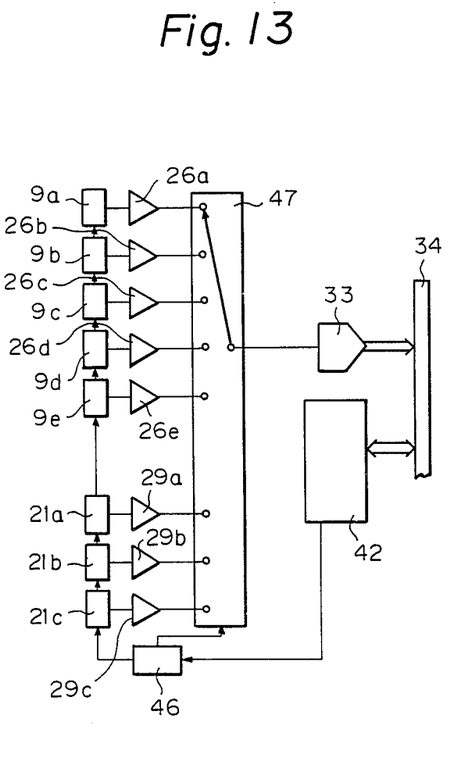
FIG. 13 is a block diagram of a heat amplifier constituting another embodiment.

FIG. 13 shows another embodiment of the head amplifier device wherein the same components as those in FIG. 9 are represented by the same numbers. In this embodiment a detecting element driving circuit 46 replaces the foregoing two driving circuits 28, 31, and the signals from all the amplifiers 26a-26e, 29a-29c are supplied to an analog multiplexer (MPX) 47 which replaces the MPXI 27, MPXII 30 and MPXIII 32, thus achieving further compactization.

Figure 14:
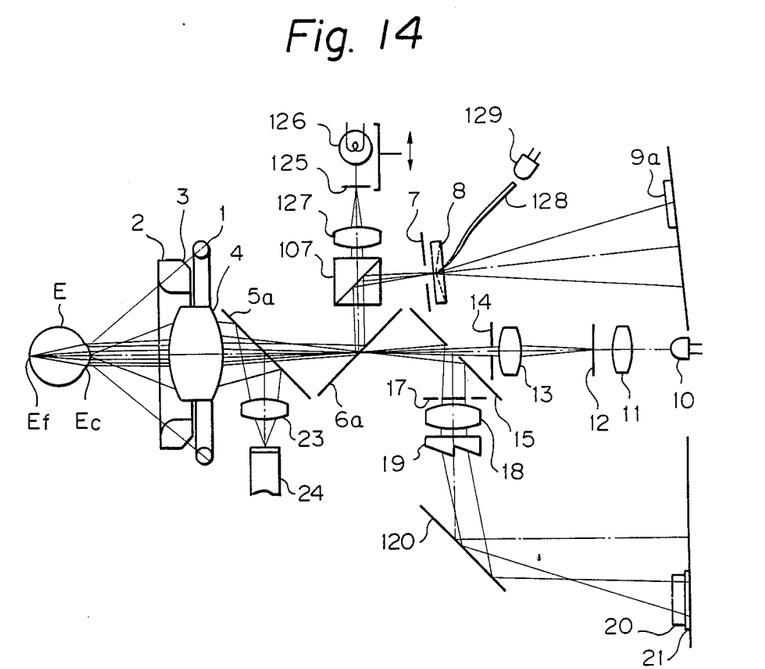
FIG. 14 is a view of an optical system of an embodiment provided with contact lens selecting function.

FIG. 14 shows the optical construction of another embodiment enabling the examinee to select an appropriaate contact lens in a rapid and exact manner, wherein the same components as those in FIG. 1 are represented by the same numbers.

In FIG. 14 there are provided a dichroic mirror 5a for reflecting near-infrared light only and transmitting light of other wavelength regions, and a dichroic mirror 6a for reflecting visible light and transmitting infrared light, whereby loss of light is prevented by selecting the wavelengths for the light for measuring the corneal shape, for measuring the eye refractive power, for alignment and for sight fixing.

A sight fixation target 125 for eye refraction measurement is provided, together with a light source 126, movably above a beam splitter 107, and, said target 125, illuminated by said light source 126, is viewed by the eye E to be examined through a relay lens 127 and the beam splitter 107 to fix said eye E.

Also an end of a fiber 128, functioning as a sight fixation target for corneal shape measurement, is positioned at the center of the prism 8 provided at the emmetropia position of the eye fundus Ef of said eye E, and a light-emitting diode 129 emitting visible light is provided close to the other end of said fiber. At the measurement of the corneal shape, the light-emitting diode 129 is turned on to emit light from the fiber 128 positioned at the center of the prism 8, whereby the eye E is fixed by viewing a clear point of light. Also, it is to be noted that certain target 125 may be suitably moved and used as a target for the corneal shape measurement.

Figure 15:
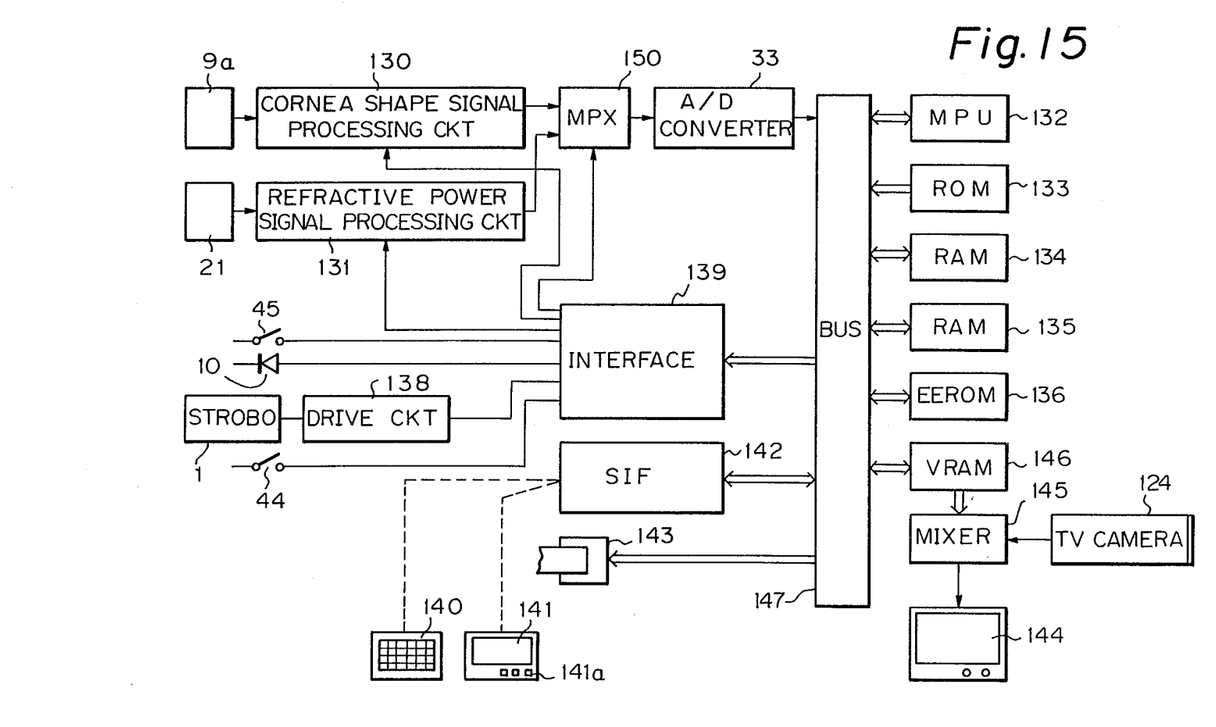
FIG. 15 is a block diagram of an electric control circuit.

FIG. 15 is a block diagram of an electrical control circuit, in which the same components as those in FIG. 1 or 14 are represented by the same numbers. To an internal bus 147 there are connected in parallel manner a corneal shape signal processing circuit 130 for receiving the signal from the detecting element 9a; an eye refraction signal processing circuit 131 for receiving the signal from the detecting element 21; a microprocessor unit (MPU) 132 for performing calculation and control; a read-only memory (ROM) 133; a first random access memory (RAMI) 134; a second random access memory (RAMII) 135 storing the information of contact lenses; an electrically erasable read-only memory (EEROM) 136 rewritably storing a table of contact lenses corresponding to the average radius of corneal curvature; an interface (IF) 139 which is connected to the corneal shape signal processing circuit 130 and the eye refraction signal processing circuit 131 for selecting said circuits through a multiplexer 150, and is further connected to the measuring switch 45, the light source 10 and a strobo driving circuit 138 connected to a ring strobo light 1; a serial interface (SIF) 142 which can be connected, when required, to an input device 140 for entering data required for preparing the table of contact lenses and to a display unit 141 for displaying the information on the selected contact lens; a printer 143 for printing the results of measurements and the information on the selected contact lens; and a video random access memory (VRAM) 146 storing the results of measurements and connected to a mixer (MIX) 145 for displaying the result of measurements and the information from the television camera 124 on a television monitor 144.

At the measurement an adjustment is carried out, with reference to the appearance of the examined eye E displayed on the television monitor 144. It is assumed that a mode of consecutive measurements of corneal shape and eye refraction, R→K or K→R, is selected by the measuring mode selector switch 44 shown in FIG. 9 or 11.

Then, in response to the actuation of the measuring switch 45, a signal from the IF 139 activates the strobo driving circuit 138 to emit light from the ring strobo light 1. The corneal reflection image formed by said light is formed on the detecting element 9a, and a signal therefrom is subjected to wave forming in the corneal shape signal processing circuit 130, then amplified in an amplifier (not shown) and converted into digital signal by the A/D converter 33, and stored in the RAM 134.

Then the light-emitting diode 10 is activated to project the chart 12 onto the eye fundus Ef, and a reflection image therefrom is focused on the detecting element 21. An output signal thereof is subjected to wave forming in the eye refraction signal processing circuit 131, then converted into an amplified digital signal through an amplifier (not shown) and the A/D converter 33 and stored in the RAM 134. When the signals of the reflection images from the cornea Ec and eye fundus Ef are stored in the RAM 134, the MPU 132 calculates, according to the equations stored in the ROM 133, the maximum, minimum and average radii of curvaturedegree of corneal astigmatism and angle of axis of astigmatism representing information on the shape of cornea, and the spherical refractive power, degree of astigmatism and angle of axis thereof representing information on the eye refractive power, and the results of these calculations are displayed on the television monitor 144 through the VRAM 146 and MIX 145. Subsequently a contact lens corresponding to the average redius of corneal curvature is selected from a table stored in the EEROM 136. The information of contact lenses stored in said EEROM 136 can be replenished or corrected through the input device 140.

Figure 16:
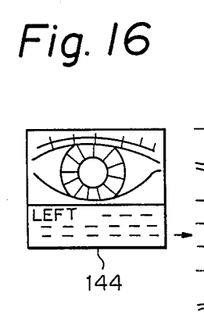
FIG. 16 is a schematic view of a display on a television monitor.

FIG. 16 shows a mode of display on the television monitor 144, in which an upper part shows the external part of the eye E to be examined, while a lower part displays the information on the corneal shape and the refractive power of the eye.

Figure 17:
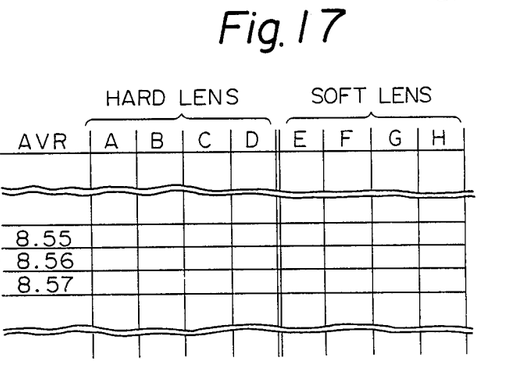
FIG. 17 is a schematic view of a contact lens selecting table stored in an EEROM.

FIG. 17 is a table of contact lenses of various manufacturers classified by the average radius AVR of the corneal curvature, registering hard contact lenses of manufacturers A-E and soft contact lenses of manufacturers E, F for each average radius AVR of the corneal curvature. For a calculated average radius of corneal curvature for example of 8.56 mm, a row indicated by arrow is selected in FIG. 17.

Then the degree of lenticular astigmatism Cr obtained by subtracting the corneal astigmatism Ck from the total astigmatism Cf, and the angle AXr of corresponding axis are determined from the following equations:

$$AXr = (1/2)\tan^{-1} \frac{(Cf \sin 2AXf - Ck \sin 2AXk)}{(Cf \cos 2AXf - Ck \cos 2AXk)}$$

wherein
AXf is the angle of axis of total astigmatism, and
AXk is the angle of axis of corneal astigmatism.

A hard contact lens or a soft contact lens is selected according to the degree Cr of lenticular astigmatism and the degree Cf of total astigmatism.

Figure 18:
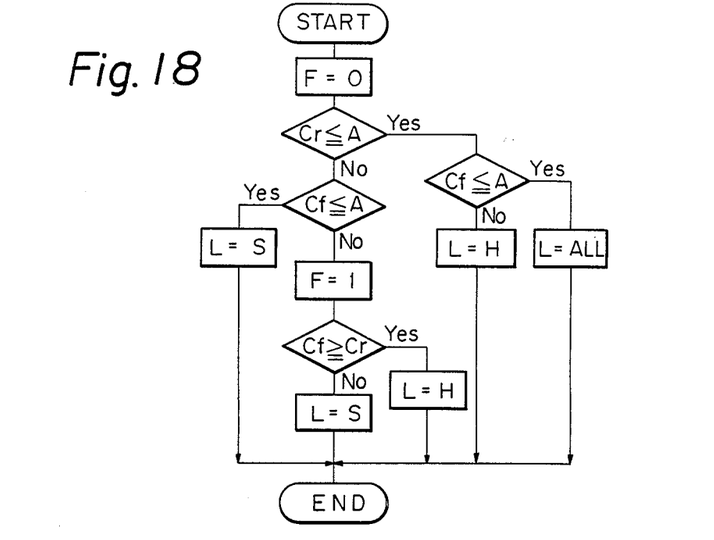
FIG. 18 is a flow chart showing the procedure of contact lens selection.

FIG. 18 is a flow chart of a procedure, to be stored in the ROM 133, for determining whether to select a hard contact lens or a soft contact lens, wherein L indicates the species of the contact lens, and L=H, L=S and L=ALL respectively indicate the selection of a hard contact lens, a soft contact lens and either one. F is a flag indicating the possibility of astigmatism correction, wherein F=0 and F=1 respectively indicate the cases of correction possible and impossible. A is a value indicating the degree of astigmatism determining the selection of the contact lens, and is usually selected as 2-3 diopters but can be changed through the input device 140.

In the following there will be explained the meaning of said flow chart. If Cr≦A and Cf≦A, the lenticular astigmatism and the total astigmatism are both small so that the corneal astigmatism Ck is also small. In the use of a hard contact lens, the corneal astigmatism is corrected, and the remaining astigmatism is not a problem as it is governed by the lenticular astigmatism Cr which is small. The use of a soft contact lens also poses no problem, since the total astigmatism is small though the corneal astigmatism is not corrected.

In case of Cr≦A and Cf>A, representing a case of a weak lenticular astigmatism Cr and a strong total astigmatism Cf. In this case the strong corneal astigmatism Ck can be corrected with a hard contact lens (L=H).

If Cr>A and Cf≦A, representing a case of a strong lenticular astigmatism Cr and a weak total astigmatism Cf. In such a case the corneal astigmatism Ck and the lenticular astigmatism Cr mutually compensate. Therefore, in order to preserve the corneal astigmatism Ck, a soft contact lens is selected (L=S).

In case of Cr>A and Cf>A, the lenticular astigmatism Cr and the total astigmatism Cf are both strong but the corneal astigmatism Ck is weak. If Cf≦Cr in this case, the corneal astigmatism Ck is manifested though it is small, the use of a hard contact lens is effective to a certain extent. On the other hand, if Cr>Cf, the corneal astigmatism is supposed to be correcting the lenticular astigmatism, and the use of a soft contact lens is desirable in order to preserve said correcting effect. Thus L=H in case of Cr>A, Cf>A and Cf≦Cr, and L=S in case of Cr>A, Cf>A and Cr>Cf.

Figure 19A:
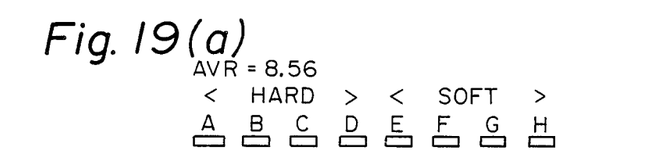
FIGS. 19(a) through 19(c) are schematic views showing the output of a selected contact lens.
Figure 19B:
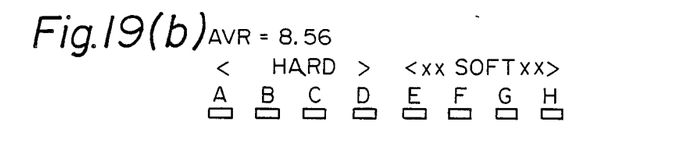
Figure 19C:
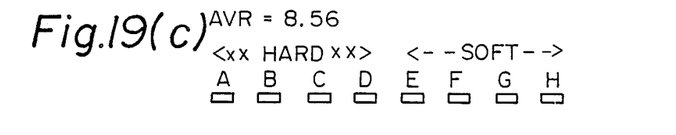

The flow chart shown in FIG. 18 represents the above-mentioned selections, and FIGS. 19(a) through 19(c) shown examples of the output of a finally selected contact lens. FIG. 19(a) shows a case of L=ALL in which a soft or hard contact lens may be employed, while 19(b) shows a case of L=H in which a hard contact lens is recommended, and (c) shows a case of F=1 and 19 still L=S so that a soft contact lens is recommended. In these example the selection of the contact lenses are indicated by symbols, but it can also be indicated by characters. Said result can be displayed on the printer 143 or the television monitor 144, or both if necessary.

Simultaneously said result is stored in the RAM 135. If required, the display unit 141 is connected to the SIF 142 and a switch 141a of said display unit 141 is actuated to display the information stored in the RAM 135, in case of prescribing a contact lens separately from the apparatus of the present invention.

In the foregoing embodiment the selection of a hard or soft contact lens is determined according to the value of the lenticular astigmatism Cr and the total astigmatism Cf, but the flow chart can also be prepared in such a manner that the comparison is at first made with the corneal astigmatism $C_k$, then the lenticular astigmatism $C_r$ and finally the total astigmatism $C_f$.

What is claimed is:

1. An ophthalmic measuring apparatus comprising:
   means for projecting a first target image onto the cornea of an eye to be examined;
   a first photodetector means;
   means for receiving a corneal reflection image of said first target image with said first photodetector means to obtain information on the corneal shape of the eye;
   means for projecting a second target image onto an eye fundus of the eye;
   a second photodetector means;
   means for receiving an eye fundus reflection image of said second target image with said second photodetector means to obtain information on the refractive power of the eye;
   signal processing means for calculating the shape of the cornea and the refractive power of the eye by receiving the output of said first photodetector means and said second photodetector means;
   said signal processing means including means for providing an output signal indicating at least a degree of remaining astigmatism $C_r$ obtained by subtracting a corneal astigmatism $C_k$ of the eye from total astigmatism $C_f$ of the eye; and
   contact lens selecting means for selecting a contact lens matching the eye to be examined, based on the output signal of said signal processing means.

2. An ophthalmic measuring apparatus according to claim 1, wherein said first photodetector means is provided with at least five linear optical position detector means for detecting positions of at least five points of said corneal reflection image.

3. An ophthalmic measuring apparatus according to claim 1, wherein said second photodetector means is provided with three linear optical position detector means in order to detect the interval of two separate light fluxes in three meridian directions.

4. An ophthalmic measuring apparatus according to claim 2, further comprising the same member of amplifiers as the number of said linear optical position detector means, in the vicinity of said linear optical position detector means.

5. An ophthalmic measuring apparatus according to claim 3, further comprising the same number of amplifiers as the number of said linear optical position detector means, in the vicinity of said linear optical position detector means.

6. An ophthalmic measuring apparatus according to claim 1, wherein said signal processing means comprises memory means for storing digital signals corresponding to said eye fundus reflection image and digital signals corresponding to said corneal reflection image respectively in separate areas.

7. An ophthalmic measuring apparatus according to claim 1, wherein said signal processing means is adapted to store one of the signals corresponding to said eye fundus reflection image and corneal reflection image and then to store the other signal, and to effect said calculations by reading said signals in succession.

8. An ophthalmic measuring apparatus according to claim 7, wherein said signal processing means comprises means for displaying the output result of said calculating means.

9. An ophthalmic measuring apparatus comprising:
   means for projecting a first target image onto the cornea of an eye to be examined;
   a first photodetector means;
   means for receiving a corneal reflection image of said first target image with said first photodetector means to obtain information on the corneal shape of the eye;
   means for projecting a second target image onto an eye fundus of the eye;
   a second photodetector means;
   means for receiving an eye fundus reflection image of said second target image with said second photodetector means to obtain information on the refractive power of the eye;
   signal processing means for calculating the shape of the cornea or the refractive power of the eye by selectively receiving the output of said first photodetector means and said second photodetector means;
   said signal processing means including means for providing an output signal indicating at least a degree of remaining astigmatism $C_r$ of the eye obtained by subtracting a corneal astigmatism $C_k$ of the eye from a total astigmatism $C_f$ of the eye;
   measuring mode selector means connected to said signal processing means to select a single measurement of the corneal shape or the eye retractive power, or successive measurements of both; and
   contact lens selecting means for selecting a contact lens matching the eye to be examined, based on the output signal of said signal processing means.

10. An ophthalmic measuring apparatus according to claim 9, wherein said contact lens selecting means is adapted to select a contact lens, based on the average radius of corneal curvature of the eye to be examined.

11. An ophthalmic measuring apparatus according to claim 10, wherein said contact lens selecting means is adapted to select a contact lens, base on the degree of corneal astigmatism and the degree of eye refraction astigmatism of the eye to be examined.

12. An ophthalmic measuring apparatus according to claim 1, wherein said contact lens selecting means is adapted to select a hard contact lens or a soft contact lens.

13. An ophthalmic measuring apparatus according to claim 9, wherein said contact lens selecting means comprises control means capable of editing, such as correction or addition on the already registered information of contact lenses.

14. An ophthalmic measuring apparatus according to claim 9, wherein said contact lens selecting means is adapted to display the output result on a printer or a television monitor.

15. An ophthalmic measuring apparatus according to claim 9, wherein said contact lens selecting means comprises memory means for storing said output result.

16. An ophthalmic measuring apparatus comprising:
    means for projecting a first target image onto the cornea of an eye to be examined;
    a first photodetector means;
    means for receiving a corneal reflection image of said first target image with said photodetector means to obtain information on the corneal shape of the eye;
    first amplifying means for amplifying said corneal reflection image of said first target image;
    means for projecting a second target image onto an eye fundus of the eye;
    a second photodetector means;

means for receiving an eye fundus reflection image of said second target image with said second photodetector means for obtaining information on the refractive power of the eye;

second amplifying means for amplifying an eye fundus reflection image of said second target image;

common signal processing means for calculating the shape of the cornea and the refractive power of the eye by receiving the output of said first and second amplifying means;

said common signal processing means including means for providing an output signal indicating at least a degree of remaining astigmatism $C_r$ of the eye obtained by subtracting corneal astigmatism $C_k$ of the eye from total astigmatism $C_f$ of the eye; and contact lens selecting means for selecting a contact lens matching the eye to be examined, based on the output signal of said signal processing means.

17. An ophthalmic measuring apparatus comprising:

means for projecting a first target image onto the cornea of an eye to be examined;

means for receiving a corneal reflection image of said first target image to obtain information on the corneal shape of the eye;

means for projecting a second target image onto an eye fundus of the eye;

means for receiving an eye fundus reflection image of said second target to obtain information on the refractive power of the eye;

photodetector means to detect said corneal reflection image and said eye fundus reflection image;

signal processing means for calculating the shape of the cornea and the refractive power of the eye by receiving the output of said photodetector means, said signal processing means including means for providing an output signal indicating at least a degree of remaining astigmatism $C_r$ obtained by subtracting a corneal astigmatism $C_k$ of the eye from total astigmatism $C_f$ of the eye; and contact lens selecting means for selecting a contact lens matching the eye to be examined based on the output signal of said signal processing means.

18. An ophthalmic measuring apparatus comprising:

means for projecting a first target image onto the cornea of an eye to be examined;

means for receiving a corneal reflection image of said first target image to obtain information on the corneal shape of the eye;

means for projecting a second target image onto an eye fundus of the eye;

means for receiving an eye fundus reflection image of said second target image to obtain information on the refractive power of the eye;

photodetector means to detect said corneal reflection image and said eye fundus reflection image;

signal processing means for calculating the shape of the cornea or the refractive power of the eye by selectively receiving the output of said photodetector means; said signal processing means including means for providing an output signal indicating at least a degree of remaining astigmatism $C_r$ of the eye obtained by subtracting a corneal astigmatism $C_k$ of the eye from total astigmatism $C_f$ of the eye;

measuring mode selector means connected to said signal processing means to select a single measurement of the corneal shape or the eye refractive power, or successive measurements of both; and contact lens selecting means for selecting a contact lens matching the eye to be examined based on the output signal of said signal processing means.

19. An ophthalmic measuring apparatus comprising:

means for projecting a first target image onto the cornea of an eye to be examined;

means for receiving a corneal reflection image of said first target image to obtain information on the corneal shape of the eye;

means for projecting a second target image onto an eye fundus of the eye;

means for receiving an eye fundus reflection image of said second target image to obtain information on the refractive power of the eye;

photodetector means to detect said corneal reflection image and said eye fundus reflection image; and signal processing means for calculating the shape of the cornea and the refractive power of the eye by receiving the output of said photodetector means, said signal processing means including means for providing an output signal indicating at least a degree of remaining astigmatism $C_r$ obtained by subtracting a corneal astigmatism $C_k$ of the eye from total astigmatism $C_f$ of the eye and including means for indicating a contact lens matching the eye to be examined based on at least said degree of remaining astigmatism.

20. An ophthalmic measuring apparatus comprising:

means for projecting a first target image onto the cornea of an eye to be examined;

means for receiving a corneal reflection image of said first target image to obtain information on the corneal shape of the eye;

means for projecting a second target image onto an eye fundus of the eye;

means for receiving an eye fundus reflection image of said second target image to obtain information on the refractive power of the eye;

photodetector means to detect said corneal reflection image and said eye fundus reflection image;

signal processing means for calculating the shape of the cornea or the refractive power of the eye by selectively receiving the output of said photodetector means, said signal processing means including means for providing an output signal indicating at least a degree of remaining astigmatism $C_r$ of the eye obtained by subtracting a corneal astigmatism $C_k$ of the eye from total astigmatism $C_f$ of the eye and including means for indicating a contact lens matching the eye to be examined based on at least said degree of remaining astigmatism; and measuring mode selector means connected to said signal processing means to select a single measurement of the corneal shape or the eye refractive power, or successive measurements of both.

* * * * *

UNITED STATES PATENT AND TRADEMARK OFFICE
CERTIFICATE OF CORRECTION

PATENT NO. : 4,878,750
DATED : November 7, 1989
INVENTOR(S) : Kyoji Sekiguchi

Page 1 of 3

It is certified that error appears in the above-identified patent and that said Letters Patent is hereby corrected as shown below:

COLUMN 1
    Line 33, change "heretofor" to --heretofore--.
    Line 67, change "auto-kerato-meter" to --auto-kerometer--.

COLUMN 2
    Line 29, change "furhter" to --further--.
    Line 39, change "multi-apertued stop;" to --multi-apertured stop;--

COLUMN 3
    Line 44, change "quar-" to --quadratic--.
    Line 45, delete "dratic".

COLUMN 4
    Line 37, before "indicate" insert --22a-22f--.

UNITED STATES PATENT AND TRADEMARK OFFICE
CERTIFICATE OF CORRECTION

PATENT NO. : 4,878,750
DATED : November 7, 1989
INVENTOR(S) : Kyoji Sekiguchi

It is certified that error appears in the above-identified patent and that said Letters Patent is hereby corrected as shown below:

COLUMN 5
    Line 3, change "retractive" to --refractive--.
    Line 9, change "corresponding axis Axc," to --corresponding axis AXc,--
    Line 53, change "as" to --an--.

COLUMN 6
    Line 56, change "preferably" to --preferable--.

COLUMN 7
    Line 7, change "obtained" to --obtained by--.
    Line 67, change "28,31," to --28 and 31,--.

COLUMN 9
    Line 29, change "curvaturedegree" to --currature, degree--.
    Line 37, change "redius" to --radius--.

UNITED STATES PATENT AND TRADEMARK OFFICE
CERTIFICATE OF CORRECTION

PATENT NO. : 4,878,750
DATED : November 7, 1989
INVENTOR(S) : Kyoji Sekiguchi

It is certified that error appears in the above-identified patent and that said Letters Patent is hereby corrected as shown below:

COLUMN 9 (Cont'd)

Line 60, after "AXr=(1/2)tan$^{-1}$ $\frac{(Cfsin2AXf-Cksin2AXk)}{(Cfcos2AXf-Ckcos2AXk)}$"

insert --Cr=$\frac{Cf(sin2AXf-Ck\ sin2AXk)}{sin\ 2AXr}$ --.

COLUMN 10
Line 36, change "Cf$\leqq$Cr" to --Cf$\geqq$Cr--.
Line 43, change "Cf$\leqq$Cr," to --Cf$\geqq$Cr,--.
Line 51, change "(c)" to --19(c)--.
Line 52, delete "19".

COLUMN 11
Line 42, change "member" to --number--.

COLUMN 12
Line 27, change "retractive" to --refractive--.
Line 42, change "Claim 1" to --Claim 11--.

Signed and Sealed this

Twenty-fifth Day of August, 1992

*Attest:*

DOUGLAS B. COMER

*Attesting Officer*   Acting Commissioner of Patents and Trademarks